US010444151B2

(12) United States Patent
Barcelo et al.

(10) Patent No.: US 10,444,151 B2
(45) Date of Patent: Oct. 15, 2019

(54) SURFACE ENHANCED LUMINESCENCE ELECTRIC FIELD GENERATING BASE

(71) Applicant: Hewlett-Packard Development Company, L.P., Houston, TX (US)

(72) Inventors: Steven Barcelo, Palo Alto, CA (US); Ning Ge, Palo Alto, CA (US); Zhiyong Li, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/570,364

(22) PCT Filed: Jul. 29, 2015

(86) PCT No.: PCT/US2015/042627
§ 371 (c)(1),
(2) Date: Oct. 30, 2017

(87) PCT Pub. No.: WO2017/019057
PCT Pub. Date: Feb. 2, 2017

(65) Prior Publication Data
US 2018/0143136 A1 May 24, 2018

(51) Int. Cl.
*G01N 21/64* (2006.01)
*G01N 21/65* (2006.01)

(52) U.S. Cl.
CPC ......... *G01N 21/645* (2013.01); *G01N 21/648* (2013.01); *G01N 21/658* (2013.01); *G01N 2021/6482* (2013.01); *G01N 2021/651* (2013.01)

(58) Field of Classification Search
None
See application file for complete search history.

(56) References Cited

U.S. PATENT DOCUMENTS

| 5,717,237 | A | 2/1998 | Chi |
| 8,436,289 | B1 * | 5/2013 | Hossain ............ H01L 27/14609 250/214.1 |
| 2003/0231304 | A1 | 12/2003 | Chan et al. |
| 2009/0166222 | A1 | 7/2009 | Mirkin et al. |
| 2010/0321684 | A1 | 12/2010 | Bratkovski et al. |
| 2011/0294691 | A1 | 12/2011 | Erickson et al. |
| 2012/0154791 | A1 | 6/2012 | Kuo et al. |

(Continued)

FOREIGN PATENT DOCUMENTS

| CN | 101123277 | 2/2008 |
| CN | 101154666 | 4/2008 |

(Continued)

OTHER PUBLICATIONS

Jayawardhana, S. et al., Additional Enhancement of Electric Field in Surface-enhanced Raman Scattering Due to Fresnel Mechanism, (Research Paper), Aug. 1, 2013.

*Primary Examiner* — Edwin C Gunberg
(74) *Attorney, Agent, or Firm* — Rathe Lindenbaum LLP

(57) ABSTRACT

Provided in one example is an analyte detection apparatus that includes surface enhanced luminescence (SEL) structure. A dielectric layer underlies the SEL structure. An electric field generating base underlies the dielectric layer. The electric field generating base is to apply an electric field about the SEL structures to attract charged ions to the SEL structures.

20 Claims, 4 Drawing Sheets

(56) References Cited

U.S. PATENT DOCUMENTS

| | | | |
|---|---|---|---|
| 2012/0212732 | A1 | 8/2012 | Santori et al. |
| 2013/0003058 | A1 | 1/2013 | Van Dorpe et al. |
| 2013/0196449 | A1 | 8/2013 | Kim et al. |
| 2014/0198376 | A1 | 7/2014 | Chang et al. |
| 2014/0211196 | A1 | 7/2014 | Samuels et al. |
| 2014/0320849 | A1 | 10/2014 | Chou et al. |

FOREIGN PATENT DOCUMENTS

| | | |
|---|---|---|
| CN | 101383378 | 3/2009 |
| CN | 101388415 | 3/2009 |
| CN | 102130132 | 7/2011 |
| CN | 102472666 | 5/2012 |
| JP | 2005-077210 | 3/2005 |
| JP | 2006-138846 | 6/2006 |
| JP | 2006-275699 | 10/2006 |
| JP | 2010107496 | 5/2010 |
| JP | 2012-073101 | 4/2012 |
| TW | 201250231 A | 12/2012 |
| TW | 201333449 A | 8/2013 |
| TW | 201416669 A | 5/2014 |
| TW | 201428268 A | 7/2014 |
| WO | WO-02074899 | 9/2002 |

\* cited by examiner

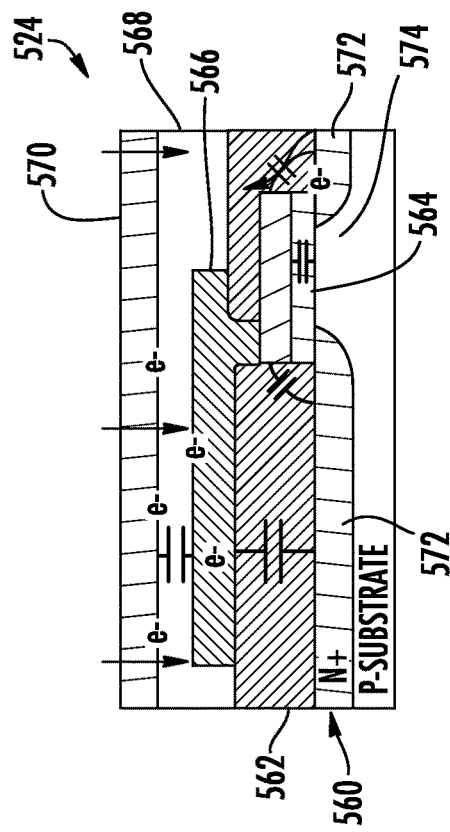
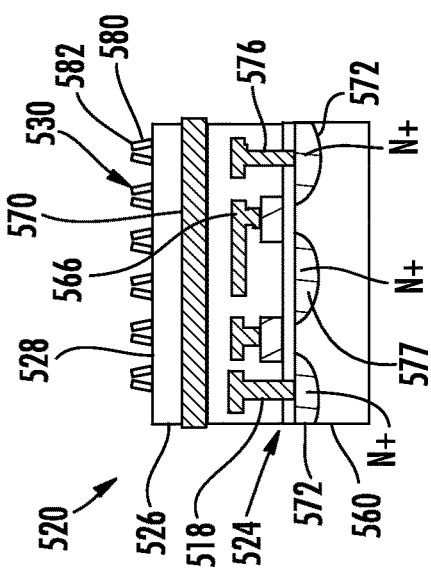
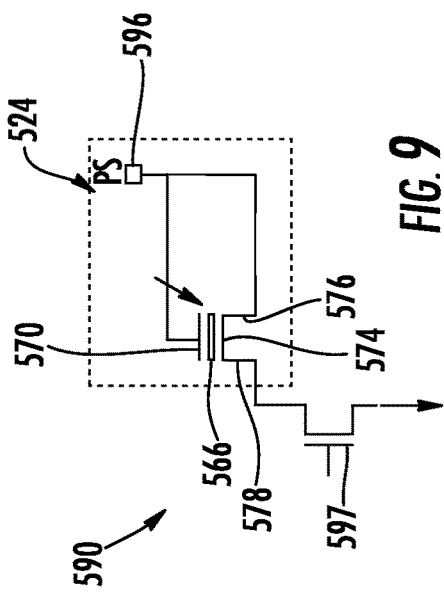
FIG. 8
FIG. 7
FIG. 9

SURFACE ENHANCED LUMINESCENCE ELECTRIC FIELD GENERATING BASE

BACKGROUND

Surface enhanced luminescence (SEL) is sometimes used for analyzing the structure of inorganic materials and complex organic molecules. SEL focuses electromagnetic radiation or light onto an analyte or solution containing an analyte, wherein the interaction between the light and the analyte is detected for analysis.

BRIEF DESCRIPTION OF THE DRAWINGS

FIG. 7 is a sectional view of another example SEL platform.

FIG. 8 is an enlarged sectional view of an electric field generating base of the platform of FIG. 7.

FIG. 9 is a diagram of a circuit for controlling an example electric field generating base.

DETAILED DESCRIPTION OF EXAMPLES

Figure 1:
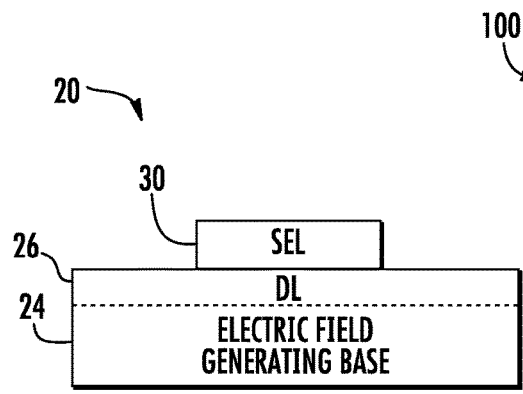
FIG. 1 is a schematic diagram of an example surface enhanced luminescence (SEL) platform.

FIG. 1 schematically illustrates an example surface enhanced luminescence (SEL) platform 20. For purposes of this disclosure, "surface enhanced luminescence" embraces within the scope of its meaning surface-enhanced Raman emission, as in surface enhanced Raman spectroscopy (SERS), and surface enhanced fluorescence. Platform 20 facilitates analysis of analytes in a solution through the use of surface enhanced luminescence. Platform 20 facilitates the generation or establishment of an electric field to attract charged ions of the analyte to surface enhanced luminescence structures to increase a density of the analyte on or adjacent the surface enhanced luminescence structures. Increasing the density of the analyte proximate to the surface enhanced luminescence structures may improve performance of surface enhanced luminescence.

Platform 20 comprises electric field generating base 24, dielectric layer 26 and surface enhanced luminescence (SEL) structure 30. Electric field generating base 24 may be dual purposed: (1) serving as a substrate for dielectric layer 26 and SEL structure 30 and (2) serving as a device to generate and apply an electric field to SEL structure 30, wherein the electric field attracts charged ions of analyte to the SEL structure 30. Platform 20 provides a programmable localized field enhanced area through device programming under a sensing area. In use, platform 20 is positioned proximate to, or provided as part of, a larger package including, a counter electrode which cooperates with base 24 to generate or form the electric field that attracts the charged ions of the analyte to the SEL structure 30. In one implementation, the electric field generating base includes circuitry that facilitates electrical charging and discharging of base 24. In one implementation, electric field generating base comprises an integrated transistor to facilitate control of the electrical charging and discharging of base 24.

In one implementation, the electric field generating base includes circuitry that facilitates the storage of electrical charge after electric field generating base 24 is no longer connected to a battery, outlet or other source of electrical current or power. In one implementation, the electric field generating base includes circuitry that facilitates the continuous provision of electrical charge about and through metal floor 28 as well as about SEL structure 30 while base 24 is no longer connected to a battery, outlet or other source of electrical current. In other words, the electric field generating base is nonvolatile. In one implementation, electric field generating base includes circuitry that forms a capacitor to store electric charge. In one implementation, base 24 comprises a floating gate MOSFET transistor (FGMOS), wherein the floating gate is charged and stores electrical charge. In one implementation, base 24 comprises a floating gate transistor in the form of a programmable read-only memory (PROM), sometimes also referred to as a one-time programmable non-volatile memory, field programmable read-only memory or floating gate avalanche injection MOS (FAMOS). In implementations were base 24 comprises a PROM floating gate transistor, the floating gate is programmed or charged by biasing the drain to avalanche so as to inject electrons into the floating gate. In contrast to other types of floating gate transistors, such as erasable programmable read-only memory transistors (EPROM), a PROM floating gate transistor omits a control gate.

In another implementation, base 24 comprises a floating gate transistor in the form of an erasable programmable read-only memory (EPROM) chip or device, facilitating the forming of platform 20 using pre-existing commercially available componentry such as commercially available EPROM chips. In some implementations, metal floor 28 and SEL structure 30 (and possibly dielectric layer 26) are formed directly upon a commercially available EPROM chip. In some implementations, metal floor 28 and SEL structure 30 (and possibly dielectric layer 26) are stamped upon the commercially available EPROM chip.

Dielectric layer 26 comprises a layer of electrically insulative or electrically non-conductive material supported above base 24 between base 24 and SEL structure 30 to two electrically insulate are separate base 24 and SEL structure 30. In one implementation, dielectric layer 26 comprises an oxidized layer of material. In one implementation, dielectric layer 26 comprises a layer of material such as silicon dioxide, silicon nitride, silicon carbon or mixtures thereof. In one implementation, dielectric layer 26 is deposited upon base 24 prior to the provision of or formation of SEL structure 30 upon dielectric layer 26. In another implementation, dielectric layer 26 is provided as a top or upper surface of base 24. Dielectric layer 26 is sufficiently thin and is formed from an appropriate material such that the electric charge produced by electric field generating base 24 passes through and across dielectric layer 26 to create an electric field about SEL structure 30.

SEL structure 30 comprises a structure that serve as a stage upon which analyte deposits, wherein the SEL structure 30 enhances the intensity of the radiation scattered or reemitted by the analyte. Structure 30 may enhance the amount of radiation or the number of photons that are scattered or re-emitted by the analyte upon being impinged by radiation from a radiation source. In one implementation, structure 30 comprises an SEL structure or a group of SEL structures within chamber 40 upon which and about analyte 24 contacts. In one implementation, the SEL structures comprise enhanced fluorescence spectroscopy structures or surface enhanced Raman spectroscopy (SERS) structures. Such structures may include a metal surface or structure, wherein interactions between the analyte and the metal surface cause an increase in the intensity of the Raman-scattered radiation. Such metal surfaces may include a roughened metal surface, such as periodic gratings. In another implementation, such metal surfaces may comprise assemble nanoparticles. In some implementations, such metal surfaces may comprise metal islands. In one implementation, such metal islands comprise flexible columnar supports such as pillars, needles, fingers, particles or wires. In some implementations, the flexible columnar structures may include a metal cap or head upon which an analyte may be deposited. In some implementations, such columnar structures are formed from materials and/or are dimensioned so as to bend or flex towards and away from one another in response to applied electric fields. In some implementations, the SERS structures are movable and are self-actuating, wherein such columnar structures bend or flex towards one another in response to micro-capillary forces so as to self-organize, wherein such bending facilitates close spacing between the structures for greater scattered radiation intensity.

In some implementations, the columnar structures are electrically conductive such that the columnar structures and/or their metal caps or heads provide distinct charging points intensifying the generated electric field at distinct points to enhance attraction of the charged ions of the analyte to the columnar structures of structure 30. For example, in some implementations, the columnar structures are formed from an electrically conductive polymer such as Poly(3,4-ethylenedioxythiophene) or PEDOT (or sometimes PEDT), a conducting polymer based on 3,4-ethylenedioxythiophene or EDOT monomer. In one implementation, the SEL or SERS structures have a nanometer scale to facilitate nano-enhanced Raman spectroscopy (NERS). Such nano-scale NERS structures may increase the intensity of radiation scattered by the analyte adsorbed on such structures by a factor as high as $10^{16}$. In yet other implementations, such columnar structures may be formed from non-electrically conductive materials, such as non-electrically conductive polymers, or may be formed from metal materials, such as wire filaments or the like.

Overall, platform 20 provides an integrated assembled unit that concurrently provides both the stage for analyte as well as the generation of electric field to attract charge molecules of the analyte to the SEL structure 30 for enhanced analyte detection. In some implementations, platform 20 is used with a separate counter electrode. In other implementations, platform 20 serves as a support for a housing so as to form an analyte detection package. In some implementations, the housing of the package itself provides or supports the counter electrode.

Figure 2:
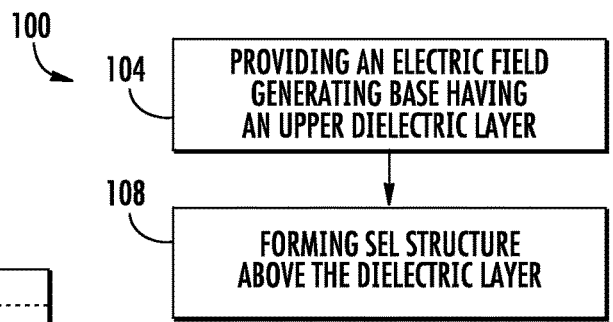
FIG. 2 is a flow diagram of an example method for forming the platform of FIG. 1.

FIG. 2 is a flow diagram of an example method 100 for forming SEL platform 20. As indicated by block 104, electric field generating base 24 having upper dielectric layer 26 is provided. The electric field generating base 24 along with dielectric layer 26 serve as a base or substrate upon which the remaining components of platform 20 may be bonded thereto, molded thereupon, stamped thereupon or otherwise formed and joined to base 24.

As indicated by block 106, metal floor 28 is formed upon dielectric layer 26. In one implementation, metal floor 28 is formed by coating dielectric layer 26 with the metal of metal floor 28. In another implementation, floor 20 is formed by evaporating metal onto dielectric layer 26. In other implementations, metal floor 20 may be formed upon dielectric layer 26. In some implementations, dielectric layer 26 is formed upon metal floor 28, wherein dielectric layer 26 is then deposited formed upon base 24.

As indicated by block 108, SEL structure 30 is formed on base 24 and dielectric layer 26. In implementations where structure 30 comprises periodic gratings, the roughened surface or periodic gratings are formed using any suitable material removal techniques such as etching and the like. In implementations where structure 30 comprises columnar structures, such columnar structures may be grown. For example, nano wire seeds may be deposited onto metal floor 28 and/or dielectric layer 26, wherein columnar structures are grown through chemical vapor deposition from a material such as silane. In another implementation, the columnar structures of structure 30 may be formed by etching the substrate. For example, in one implementation, a reactive ion etching process may be applied to a substrate, such as a silicon, producing flexible columns. The material removal from the silicon substrate may be achieved through the action of reactive gaseous species such as fluorine, chlorine, bromine or a halogen, in the presence of gaseous nitrogen, argon or oxygen. In yet another implementation, such columnar structures may be formed by nano printing, wherein a thin-film, such as a polymer capable of significant cross-linking under exposure to UV light, is applied to floor 28, in the form of a web to produce a coating on the web and wherein flexible columns in the form of nanopoles are produced by rolling the web between a pair of rolls, one of which is a die having a relief pattern that is impressed into the highly viscous thin film coating of the web leaving a negative of the relief pattern of the die in the form of a plurality of nano poles on the web. In yet another implementation, hot nano embossing of a coating, such as a polymer plastic, with a die having a relief pattern that is impressed into the polymer plastic that coats the substrate so as to leave a negative of the relief pattern of the die in the form of a plurality of nano poles on the substrate.

The metal heads or caps on the columnar structures may be formed utilizing a process such as precipitation of a metal onto the structures from a colloidal suspension of metallic nano particles, lifting of portions of a deposited metallic layer to form a metallic cap or reducing adsorbed the metalo-organic compounds by energetic particle bombardment. In one implementation, a stream of metal vapor may be produced using thin film vacuum evaporation techniques to deposit metal onto each of the columnar supports.

In yet another implementation, the metallic caps may be formed using electroplating process in which the flexible columns are immersed in a plating solution containing metal cations. The application of an electrical potential to the columnar structures results in an enhanced electrical field at the apices of the flexible columns. The electrical field attracts the metal cations to the apices, wherein chemical reduction of the metal cations occurs such that metal is deposited to grow the metallic caps. In still other implementations, SEL structure 30 may be formed using other processes.

Figure 3:
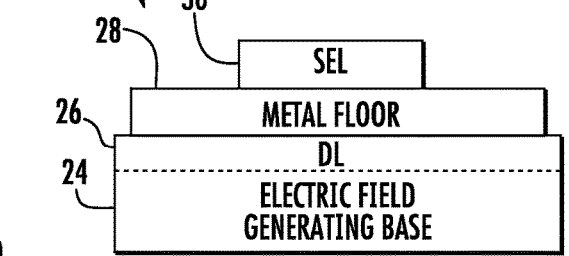
FIG. 3 is a schematic diagram of another example SEL platform.

FIG. 3 schematically illustrates SEL platform 120, an example implementation of SEL platform 20. SEL platform 120 is similar to platform 20 except that SEL platform 120 additionally comprises metal floor 28. Metal floor 28 comprises floor or layer of metal material to enhance surface enhanced luminescence. Metal floor 28 is supported by dielectric layer 26 and the underlying base 24. In one implementation, metal floor 28 is supported directly upon dielectric layer 26. In another implementation, additional intermediate layers are disposed between dielectric layer 26 and metal floor 28. In one implementation in which SEL structure 30 comprises columnar structures such as nanofingers, during the forming of metal tips or caps metal floor 28 is formed upon such columnar structures and comprises a metal such as nickel, gold, platinum, palladium, rhodium or alloys thereof. In some implementations, metal floor 28 may additionally comprise another layer of metal such as aluminum, aluminum copper, tantalum aluminum, or tantalum aluminum with aluminum copper. For purposes of this disclosure, unless otherwise specifically noted, the term "metal" encompasses a single metal as well as alloys thereof. In one implementation, metal floor 28 has a thickness of between 50 nm and 800 nm, and nominally 300-500 nm.

Figure 4:
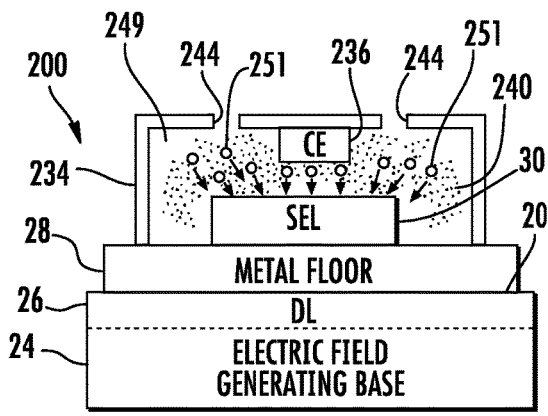
FIG. 4 is a schematic diagram of an example SEL package including the platform of FIG. 1.

FIG. 4 schematically illustrates an example SEL package 200. Package 200 comprises a self-contained unit, in which a solution containing analyte may be deposited and subsequently evaporated. In the example illustrated, package 200 provides a counter electrode for the formation of an electric field that attracts charged ions of the analyte within the solution to the structure 30 prior to the completion of evaporation of the solution. Package 200 utilizes platform 20 described above.

As further shown by FIG. 4, package 200 additionally comprises housing 234 and counter electrode 236. Housing 234 comprises a cover, lid, dome or other structure extending above floor 28 to form a chamber 240 in which a solution containing analyte may be filled or deposited. In one implementation, housing 234 extends directly from and is directly supported by metal floor 28. In yet another implementation, housing 234 extends directly from and is directly supported by dielectric layer 26. In still another implementation, housing 234 extends directly from and is directly supported by base 24. In the example illustrated, housing 234 comprises openings 244. In one implementation, openings 244 serve as fill openings through which the solution 249 containing analyte 251 is deposited into chamber 240. In one implementation, housing 234 is formed from a polymer. Another implementation, housing 234 is formed from a metal, such as nickel, where the metallic layers of housing 234, themselves, serve as counter electrode 236.

Counter electrode 236 may comprise a metal electrode supported by housing 234 at a location spaced from metal floor 28 and base 24 along chamber 240. In one implementation, counter electrode 236 is mounted to the polymer or electrically nonconductive material of housing 234. In another implementation, counter electrode 236 (schematically shown) is integrated as part of housing 234. For example, in one implementation, housing 234 may include a metal layer, such as nickel, that serves as counter electrode 236.

In operation, the electric field generating base 24 and metal layer 28 cooperate with counter electrode 236 to form an electric field through and within chamber 240. As indicated by arrows, the electric field causes charged molecules or ions of analyte 251 to be attracted to and drawn to structure 30. In one implementation, during or after movement of the analyte towards and upon structure 30, the solution 249, diluted of analyte 251 in regions distant structure 30, is evaporated or allowed to evaporate. Thereafter, light or radiation is directed towards structure 30, wherein light emanating from structure 30 as a result of interaction with analyte 251 is sensed or detected to indicate characteristics of the analyte 251. In one implementation, the radiation is directed toward structure 30 as part of a Ramen spectroscopy testing process. In another implementation, light or radiation is directed toward structure 30 as part of fluorescence testing process.

Figure 5:
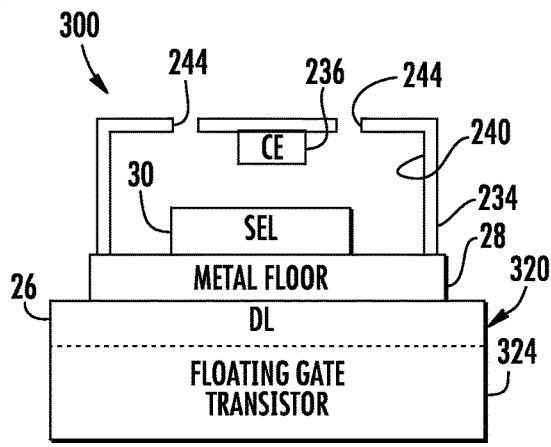
FIG. 5 is a schematic diagram of another example SEL package.

FIG. 5 schematically illustrates another example SEL package 300. Package 300 comprises a self-contained unit in which a solution containing analyte may be deposited nd subsequently evaporated. In the example illustrated, package 300 provides a counter electrode for the formation of an electric field that attracts charged ions of the analyte within the solution to the structure 30 prior to the completion of evaporation of the solution. Package 300 utilizes platform 20 described above.

Package 300 is similar to package 200 except that package 300 is specifically illustrated as comprising a floating gate transistor 324. In one implementation, the floating gate transistor comprises an erasable programmable read-only memory (EPROM) device which serves as an electric field generating base. In another implementation, the floating gate transistor comprises a programmable read-only memory (ROM) device which serves as the electric field generating base. Those remaining components or structures of package 300 which correspond to components or structures of package 200 are numbered similarly.

Floating gate transistor 324 comprises a device that is sometimes used in computers and other electronic devices to store data. In package 300, floating gate transistor 324 provides electric field generating base for platform 320. Floating gate transistor 324 comprises a floating gate that holds a charge. In package 300, the floating gate is utilized to store an electrical charge that continuously cooperates with counter electrode 236, which serves as an electrical ground, to provide an electric field within chamber 240. As a result, package 300, and in particular, the floating gate of floating gate transistor 324, may be pre-charged hours, days and even weeks prior to use of package 300. The charges stored by the floating gate of floating gate transistor 324, rendering package 300 ready for use at any time subsequent to such pre-charging. In one implementation, package 300, along with other packages 300, may be charged prior to use, such as during manufacture, prior to distribution or when inventoried prior to use. The floating gate of the floating gate transistor stores the charge such that use of package 300 involves filling chamber 240 with the solution and analyte to be tested. The electrical field, already existing as provided by the floating gate, attracts charged molecules of the analyte to structure 30 to facilitate testing. The floating gate of the EPROM device 324 facilitates testing of a solution containing analyte without package 30 itself being connected to a source of electrical current, such as a battery or power outlet.

Figure 6:
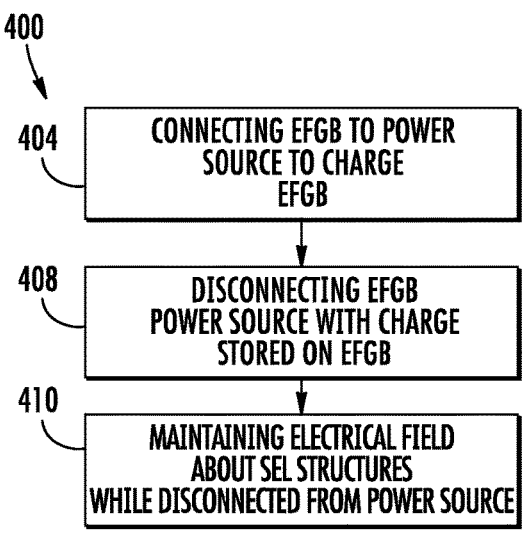
FIG. 6 is a flow diagram of an example method for using the platform of FIG. 1 or the packages of FIG. 3 or 4.

FIG. 6 is a flow diagram illustrating an example method 400 for use of package 300. As indicated by block 404, the electric field generating base, such as floating gate transistor 324, is connected to power source, such as a source of electrical current, to charge the electrical charging device. In implementations where the electrical field generating base comprises a floating gate transistor 324 in the form of an EPROM device, charging is achieved by grounding source and drain terminals and placing sufficient voltage at a control gate tunnel through an oxide to the floating gate. In implementations where the electric field generating base comprises a floating gate transistor in the form of a PROM device, charging is achieved by biasing the drain to avalanche so as to inject electrons into the floating gate.

As indicated by block 408, upon the electrical field generation base 24, such as the floating gate of the floating gate transistor 324 becoming sufficiently charged, the electric field generation base is disconnected from the power source, the source of electrical current. Upon disconnection, the electrical field generating base, such as floating gate transistor 324, stores the charge, forming a continuous or concert electric field within chamber 240. As indicated by block 410, the electrical field about structure 30 is maintained while the electrical field generating base or floating gate transistor 324 is disconnected from the source of electrical current. As a result, package 200 or package 300 is ready for use without base 24 or floating gate transistor 324 being connected to a source of electrical power or electrical current. Filling of chamber 240 with a solution containing analyte to be tested (hours, days or weeks after the initial preliminary charging of base 24 or floating gate transistor 324) may expose the solution and analyte to the electric field, resulting in charged molecules of the analyte being attracted to structure 30 where their density increases to increase the intensity of the sensed radiation from the luminescence testing (Ramen spectroscopy or fluorescence).

FIG. 7 schematically illustrates SEL platform 520, another implementation of platform 20. Platform 520 is similar to platform 20 in that platform 520 comprises an electric field generating base 524, a dielectric layer 526, metal floor 528 and an SEL structure 530. Electric field generating base 524 comprises an EPROM device. In the example illustrated, electric field generating base 524 comprises one example of floating gate transistor 324, an EPROM device, wherein electric field generating base 524 comprises an nMosfet or nMOS field effect transistor in which the channel contains electrons, opposite in type to the p type substrate, leading to a negatively charged floating gate which attracts positive ions.

FIG. 8 illustrates one example of electric field generating base 524 in detail. In the example illustrated, base 524 comprises a substrate 560, dielectric layer 562, dielectric layer 564, floating gate 566, dielectric layer 568 and control gate 570. Substrate 560 comprises a p-type silicon substrate having doped n-type regions 572 separated by a channel region 574 formed by the undoped p-type silicon substrate. Dielectric layer 562 comprises an electrically insulating layer that extends between n type regions 572 and floating gate 566. Dielectric layer 564 comprises an electrically insulating layer that spans channel 574 and extends between channel region 574 and floating gate 566. In one implementation, layers 562 in 564 are a single contiguous layer. In one implementation, layers 562 and 564 comprise phosphosilicate glass (PSG). In other implementations, layer 562 and/or layer 564 may be formed from other electrically insulating or dielectric materials including but not limited to as silicon dioxide.

Floating gate 566 may comprise a layer of electrically conductive material spaced from substrate 560 by layers 562, 564 and further spaced from and electrically insulated from control gate 570 by dielectric layer 568. In one implementation, floating gate 566 comprises a metal layer or film. In one implementation, floating gate 566 comprises tungsten or aluminum. In other implementations, floating gate 566 is formed from other metals.

Dielectric layer 568 spaces floating gate 566 from control gate 570 and insulate floating gate 566 from control gate 570. Dielectric layer 568 may comprise an electrically insulating material such an oxide such as silicon dioxide or silicon nitride. In yet other implementations, dielectric layer 568 may comprise other electrically insulating materials.

Control gate 570 comprises a metal layer metal film supported by dielectric layer 568 opposite to floating gate 566. During charging of floating gate 566, control gate 570 receives electrical current while source and drain terminals 576, 578 (shown in FIG. 7), partially provided by n-type regions 572, are grounded such that voltage on control gate 570 tunnels through dielectric 568 to floating gate 566. The charge on floating gate 566 is maintained such that floating gate 566 subsequently cooperates metal floor 528 and a counter electrode to provide static electric field about SEL structure 530.

In other implementations, the EPROM device forming electric field generating base 524 may comprise a pMOSFET or pMOS field effect transistor the in-type and P-type regions of substrate 560 shown in FIG. 8 are flipped such that the channel contains holes, opposite in type to the n type substrate, leading to a positively charged floating gate which attracts negative ions. In such an implementation, base 524 is similar to base 524 shown in FIGS. 6 and 7 except that substrate 560 comprises a n-type silicon substrate having undoped p-type regions 572 separated by a channel region 574 formed by the doped n-type silicon substrate.

Dielectric layer 526 may be similar to dielectric layer 26 described above. Dielectric layer 526 comprises an electrically insulated or dielectric layer, such as an oxide, formed between control gate 570 and metal floor 528. Metal floor 528 is similar to metal floor 28 described above. SEL structure 530 is similar to SEL structure 30 described above except that SEL structure 530 is specifically illustrated as comprising flexible columnar structures in the form of flexible nanofingers 580 having metal caps 582. In one implementation, nano fingers 580 comprise flexible polymers while metal caps 582 comprise gold, silver, platinum, rhodium or other metals.

FIG. 9 schematically illustrates an example electric circuit 590 for controlling electric field generating base 524. In the example illustrated, base 524 additionally comprises a power source 596 and selection transistor 597 to selectively control or actuate charging of the floating gate of base 524.

Figure 10:
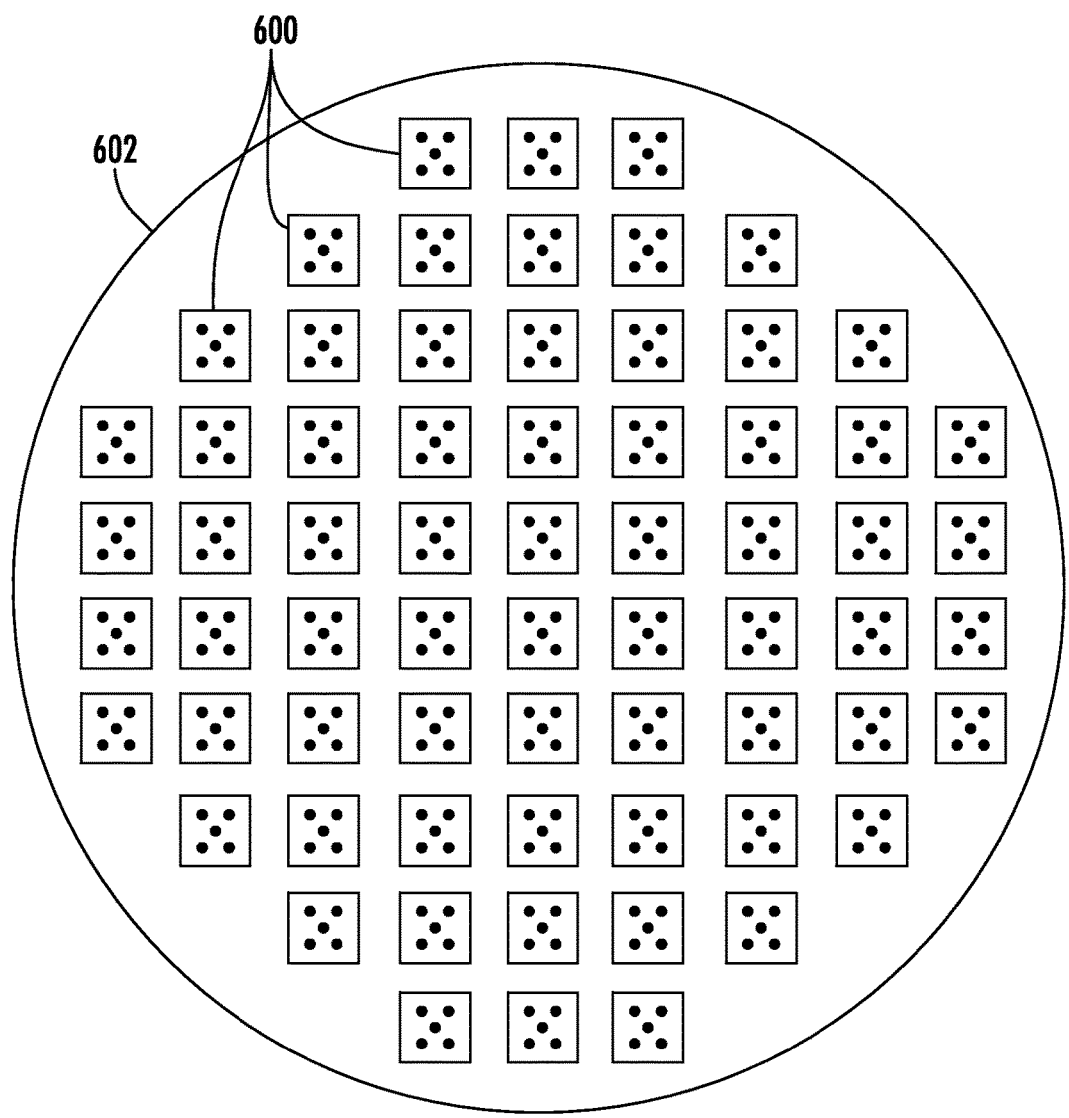
FIG. 10 is a top view of an example wafer including an array of example LES packages.

FIGS. 9 and 10 illustrate multiple SEL packages 600, example implementations of package 200. As shown by FIG. 10, packages 600 may be formed using semiconductor integrated circuit fabrication techniques as part of a wafer 602. The individual packages 600, formed as part of the wafer 602, are then subsequently separated into individual packages or individual sets of packages.

Figure 11:
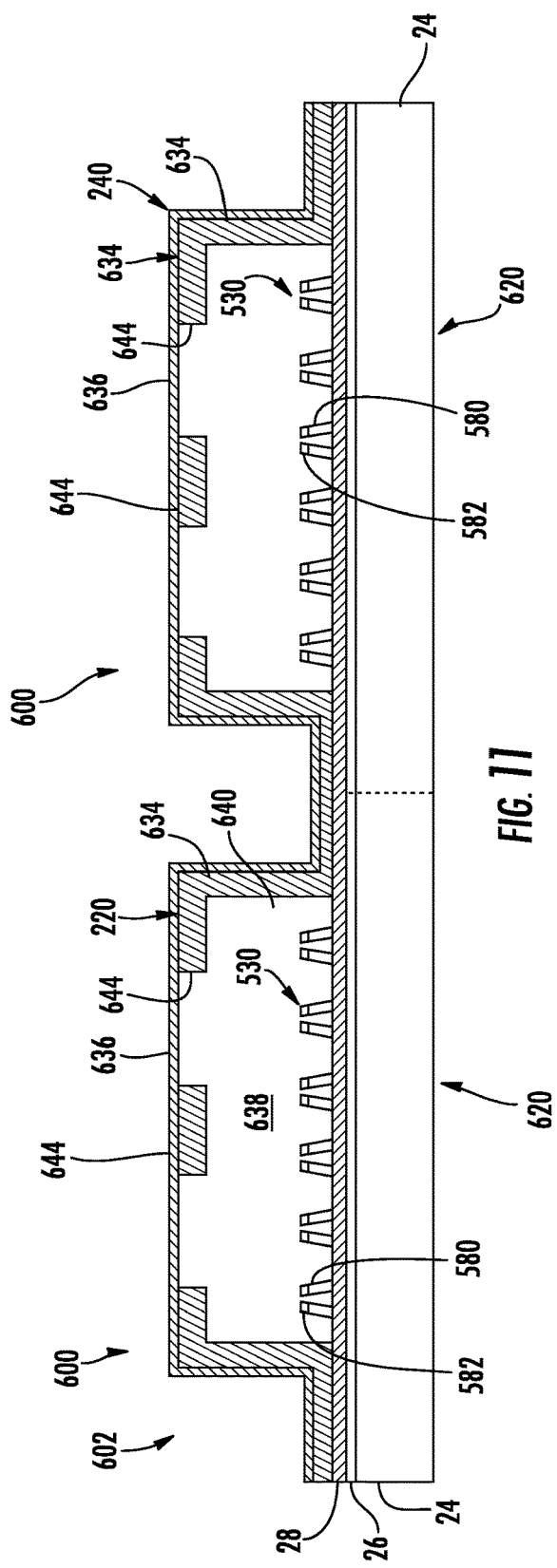
FIG. 11 is a sectional view illustrating a pair of the example packages on the wafer of FIG. 10.

FIG. 11 is a sectional view illustrating two of the packages 600 formed as part of wafer 602. For ease of discussion, one of the packages 600 is described. As shown by FIG. 11, package 600 comprises electric field generating bases 24, dielectric layer 26, metal layer 28, SEL structure 530, housing 634 and seal 636. Electric field generating bases 24, dielectric layer 26, metal layer 28 and SEL structure 530 of each of packages 600 are described above. As described above, electric field generating basis 24, dielectric layer 26, metal layer 28 and SEL structure 530 form an SEL platform 620, wherein electric field generating base 24 serve as a substrate or foundation for the rest of the platform.

Housing 634 extends from metal layer 28. In other implementations, housing 634 may contact and directly extend from dielectric layer 26 or based 24. Housing 634, sometimes referred to as an orifice plate, cooperates with metal layer 28 to form and define the interior 638 of chamber 640.

Housing 634 protects SEL structure 530 from exposure to the environment and reduces or prevents oxidation of surfaces of SEL structure 530 prior to use. Housing 634 may additionally reduce or prevent unintentional or premature exposure of SEL structure 530 to extraneous substances or an analyte that SEL structure 530 is intended to detect. Although housing 634 and platform 620 are illustrated as forming a rectangular shaped chamber 640, in other implementations, chamber 640 may have other shapes.

In one implementation, housing 634 comprise walls that are formed by selectively plating a mandrel with a layer or layers of metal and subsequently removing the mandrel to form the housing with apertures. In one implementation, housing 634 may have a metal surface such as nickel, gold, platinum or rhodium, for example. In one implementation, the walls of housing 634 are formed entirely from such a metal. In such an implementation, the walls of housing 634, being formed from metal, serve as a counter electrode, similar to counter electrode 236 described above, which together with base 24 forms a static electric field within chamber 640 about SEL structure 530. In yet other implementations, housing 634 may be formed from non-metallic materials using processes other than plating.

In the example illustrated, housing 634 further comprises fill openings 644. Fill openings 644 comprise passages extending from the exterior of package 634 to interior 638 of chamber 640. Fill openings 644 are each sized and located to facilitate filling of interior 638 with the solution containing the analyte to be tested. In the example illustrated, each of fill openings 644 extends through housing 634. As indicated by broken lines, in other implementations, package 600 may additionally or alternatively comprise other fill openings.

Seal 636 comprises a panel or layer of material coupled to a remainder of package 600 across fill openings 644. Seal 636 provides a hermetic seal to inhibit contamination of interior 638. Seal 636 inhibits oxidation of the metal surfaces within interior 638 prior to use of package 600. Seal 636 further indicates previous use of package 600. Seal 636 may be formed from a polymer tape, plastic, transparent material, plastic sheeting, foil material, foil sheeting, film, membrane, wax or polydimethylsiloxane.

When analyte is to be deposited within interior 638, seal 636 may be altered to provide access through fill openings 644. In one implementation, seal 636 is releasably or removably adhered to housing 634 by pressure sensitive adhesive or the like that allows seal 636 to be peeled away from fill openings 644. In yet another implementation, seal 636 is formed from a material and/or is dimensioned so as to be punctured through fill openings 644 and/or torn away from openings 644. In yet other implementations, seal 636 comprises a septum that allows insertion of a needle through openings 644, wherein the septum resiliently closes upon withdrawal of the needle. In yet other implementations, seal 636 is provided by a lid, top, door, hatch or cap that temporarily seals or closes openings 644. In some implementations, seal 636 is omitted.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements.

What is claimed is:

1. An analyte detection apparatus comprising:
   a surface enhanced luminescence (SEL) structure;
   a dielectric layer underlying the SEL structure; and
   an electric field generating base underlying the dielectric layer, the electric field generating base to apply an electric field about the SEL structure to attract charged ions to the SEL structure, wherein the electric field generating base comprises an integrated transistor.

2. The analyte detection package of claim 1 further comprising a metal floor from which the SEL structure extends, wherein the dielectric layer underlies the metal floor.

3. The analyte detection apparatus of claim 2 further comprising a housing above the metal floor and over the SEL structure, the housing supporting a counter electrode to facilitate the generation of the electric field.

4. The analyte detection apparatus of claim 2, wherein the housing forms a fluid chamber and wherein the counter electrode is supported within the fluid chamber.

5. The analyte detection apparatus of claim 1, wherein the electric field generating base comprises a floating gate.

6. The analyte detection apparatus of claim 5 further comprising a selection transistor to selectively control charging of the floating gate.

7. The analyte detection apparatus of claim 1, wherein the electric field generating base comprises an erasable programmable read-only memory (EPROM) chip.

8. The analyte detection apparatus of claim 1, wherein the electric field generating base comprises:
   a substrate;
   a source electrode supported by the substrate;
   a drain electrode supported by the substrate;
   a channel material between the source electrode in the drain electrode; and
   a floating gate spaced opposite the channel material between the source electrode and the drain electrode, wherein the dielectric layer is between the floating gate and the SEL structure.

9. The analyte detection apparatus of claim 1, wherein the SEL structure is part of a group of SEL structures, the SEL structure comprising a flexible columnar support.

10. The analyte detection apparatus of claim 9, wherein the flexible columnar support comprises a metal.

11. The analyte detection apparatus of claim 9, wherein each of the SEL structures is self-actuating such that the columnar structures bend towards one another in response to micro capillary forces to self-organize.

12. The apparatus of claim 1 further comprising:
   a housing forming a fluid chamber about the SEL structure and over the electric field generating base, the housing comprising fill openings; and
   a seal temporarily closing the fill openings, the seal being alterable to open the fill openings.

13. An apparatus comprising:
   an erasable programmable read-only memory (EPROM) device providing an electric field generating base;
   a dielectric layer supported by the EPROM device; and a dielectric surface enhanced luminescence (SEL) structure extending above the dielectric layer.

14. The apparatus of claim 13 further comprising a metal floor supported by the dielectric layer.

15. The apparatus of claim 14 further comprising:
a housing cooperating with the metal floor to form a chamber about the SEL structure; and
a counter electrode supported by the housing.

16. The apparatus of claim 15, wherein the housing comprises a metal layer forming the counter electrode.

17. A method comprising:
forming a surface enhanced luminescence (SEL) structure above an upper dielectric layer of an electric field generating base.

18. The method of claim 16 further comprising storing an electrical charge on the electric field generating base.

19. The method of claim 16 further comprising forming a metal floor above the dielectric layer and housing above the metal floor, the housing cooperating with the metal floor to form a chamber and supporting a counter electrode spaced from the metal floor.

20. The method of claim 16, wherein the electric field generating base comprises a floating gate transistor.

* * * * *

UNITED STATES PATENT AND TRADEMARK OFFICE
CERTIFICATE OF CORRECTION

PATENT NO. : 10,444,151 B2  
APPLICATION NO. : 15/570364  
DATED : October 15, 2019  
INVENTOR(S) : Steven Barcelo et al.

Page 1 of 1

It is certified that error appears in the above-identified patent and that said Letters Patent is hereby corrected as shown below:

In the Claims

Column 10, Line 19, Claim 2, delete "package" and insert -- apparatus --, therefor.

Column 10, Line 58, Claim 12, after "The" insert -- analyte detection --.

Column 11, Line 15, Claim 18, delete "16" and insert -- 17, --, therefor.

Column 11, Line 17, Claim 19, delete "16" and insert -- 17, --, therefor.

Column 11, Line 22, Claim 20, delete "16" and insert -- 17 --, therefor.

Signed and Sealed this  
Twenty-fifth Day of February, 2020

Andrei Iancu  
*Director of the United States Patent and Trademark Office*